United States Patent [19]

Duong-Van

[11] Patent Number: 5,439,483

[45] Date of Patent: Aug. 8, 1995

[54] METHOD OF QUANTIFYING CARDIAC FIBRILLATION USING WAVELET TRANSFORM

[75] Inventor: Minh Duong-Van, Palo Alto, Calif.

[73] Assignee: Ventritex, Inc., Sunnyvale, Calif.

[21] Appl. No.: 139,953

[22] Filed: Oct. 21, 1993

[51] Int. Cl.⁶ .................... A61B 5/046; A61N 1/36
[52] U.S. Cl. ............................ 607/5; 128/705
[58] Field of Search .............. 128/700, 702, 705; 607/4, 5, 7

[56] References Cited

U.S. PATENT DOCUMENTS 5,077,667 12/1991 Brown et al. .................. 128/703
5,262,958 11/1993 Chui et al. ..................... 364/487

OTHER PUBLICATIONS

Wavelets "Signal Representations with Important Advantages", Freeman, Optics & Photonics News Aug. 1993 pp. 8-14.

*Primary Examiner*—William E. Kamm
*Assistant Examiner*—Marianne Parker
*Attorney, Agent, or Firm*—Steven M. Mitchell; Mark J. Meltzer

[57] ABSTRACT

The present invention provides a system and method for characterizing cardiac fibrillation using wavelet transforms. By characterizing the seriousness of a fibrillation episode, a defibrillation shock may be delivered to the heart with less excess energy than conventional ICDs. A wavelet transform is performed on a digitized ECG using a second derivative weight function and the results are analyzed for missing "peaks" in the data. The more serious the fibrillation, the more peaks will be missing from the data. This information may then used to modify the voltage of the defibrillation shocks as a function of the seriousness of the fibrillation.

10 Claims, 7 Drawing Sheets

METHOD OF QUANTIFYING CARDIAC FIBRILLATION USING WAVELET TRANSFORM

FIELD OF THE INVENTION

The present invention relates generally to cardiac arrhythmia detection devices, and more specifically to a system which provides a method for characterizing cardiac fibrillation.

BACKGROUND OF THE INVENTION

The human heart is divided into four chambers, two upper chambers called atria and two lower chambers called ventricles. The heart's function is to pump blood through the body's circulatory system. A healthy heart at rest typically beats between 60 and 100 times per minute and will pump over 1,800 gallons of blood per day. Each normal heart beat is the result of electrical signals generated at a precise area in the right atrium, called the sino-atrial node, the heart's natural pacemaker. These electrical signals cause a physical contraction of the atria, which pump blood into the ventricles. The electrical impulses then continue to the ventricles, causing them to contract and distribute blood throughout the body.

Arrhythmias, abnormal rhythms of the heart muscle, arise from numerous causes, including tissue damage due to previous heart attacks, congenital defects and certain diseases. Arrhythmias can originate in either the atria where they are generally not life-threatening, or the ventricles, where they can significantly interfere with the pumping of oxygenated blood and can therefore be life-threatening. During an arrhythmia, the heart beats either too slowly or too rapidly. An abnormally slow heart rate, generally defined as a heart rate below 50 beats per minute, is known as bradycardia. This condition is usually treated by implanting a bradycardia pacemaker, a device that monitors the heart and delivers electrical impulses when necessary to increase the heart rate. A more serious arrhythmia occurs when the ventricles beat at an abnormally rapid rate, a condition known as ventricular tachycardia. In ventricular tachycardia, abnormal electrical signals occur in the ventricles. When the ventricles beat at an abnormally rapid rate, they do not have sufficient time to fill with blood prior to each contraction and therefore less blood is pumped out of the heart. As a result, less oxygen is carried to the tissues and organs of the body. This lack of oxygen can cause dizziness, unconsciousness, cardiac arrest and, ultimately, death.

Episodes of ventricular tachycardia occur unpredictably and tend to become more serious over time. Ventricular tachycardia can progress to the most serious type of cardiac arrhythmia, ventricular fibrillation. In ventricular fibrillation, the heart's normal electrical impulses become disorganized and erratic. Unlike ventricular tachycardia, during which the heart continues to contract in an organized fashion, in ventricular fibrillation the heart quivers and ceases to pump blood. As a result, the individual's blood pressure falls to nearly zero. If ventricular fibrillation is not terminated quickly, the individual will experience a sudden cardiac death (SCD) episode during which the individual will become unconscious as a result of the heart's failure to pump oxygenated blood to the body's tissues and organs, and without prompt medical intervention, typically will die.

A well-known device for treating patients with arrhythmias is an implantable cardioverter/defibrillator (ICD) which is an electronic device that is implanted in the patient and is designed to monitor the patient's heartbeat and deliver electric pulses or shocks to the heart to terminate arrhythmias. A typical ICD system consists of a device for pulse generation, defibrillation leads and pacing/sensing leads. The pulse generator contains the battery and electronic circuitry that monitors the patient's heartbeat and delivers therapy upon detection of a ventricular tachyarrhythmia. The pacing/sensing leads are insulated wires that connect the pulse generator to the heart and allow the device to sense the patient's heartbeat. These leads also carry electrical pulses for pacing. The defibrillation leads carry electrical shocks to terminate ventricular tachycardia and ventricular fibrillation. The defibrillator is surgically implanted beneath the skin in the patient's abdomen and the defibrillation leads are typically either epicardial patch electrodes connected to the exterior of the heart or endocardial leads inserted transvenously into the chambers of the heart. An endocardial lead system may also include a subcutaneous patch electrode. An ICD system of this type is described in U.S. Pat. No. 5,014,701 to Pless et al., which is assigned to the assignee of the present application and which is incorporated herein by reference.

A number of different ICD systems and methods have been developed for delivering electrical shocks to a patient's heart in response to detected arrhythmias. These methods deliver specific waveform shapes or pulse sequences to the heart in order to treat the detected arrhythmia. Different therapies may be used to treat different arrhythmias. In the case of conventional defibrillation pulses, high voltage shocks are delivered to the heart. Typically these shocks deliver an energy of from about 10 to 40 joules at a voltage of from about 500 to 1000 volts. The amount of energy delivered is determined by the patient's physician, typically by programming the voltage for the shock and the duration of either a monophasic or biphasic waveform. The programmed voltage is calculated by determining the actual defibrillation threshold of the individual patient with testing during device implant and the addition of a safety margin. The safety margin is needed for a number of reasons. First, the impedance of the leads may increase with time and this will reduce the actual energy delivered to the heart for a given voltage. Second, the threshold for defibrillation of a spontaneous fibrillation may be different from the induced fibrillation which is terminated during testing. Finally, it is typical to be conservative with safety margins when a patient's life is at stake. While this technique for programming and delivering high voltage shocks to the heart has proved effective as a lifesaving procedure, it has many drawbacks. First, defibrillation shocks are extremely painful to the patient. The lower the voltage which is effective and safe the better. Second, the high energy delivery requirements necessitates relatively large batteries and capacitors to enable delivery of the large shocks and to allow for device lifetimes of up to five years or longer. The presence of large batteries and capacitors results in a device package which may be uncomfortable for the patient, particularly for abdominal implants. A smaller device may permit pectoral implants which are more desirable for a number of know reasons. Thus, lower voltage shocks are less painful and disruptive to the patient and lower energy requirements allow for use of smaller batteries and capacitors and thus smaller implantable devices. One way of achieving this is to minimize the safety margin while still assuring successful defibrillation. Thus, it would be desirable if the necessary safety margin could be minimized.

An important feature of an ICD is the arrhythmia detection system. One of the earliest techniques for detection is described in U.S. Pat. No. Re27,757 to Mirowski in which a pressure transducer is positioned in the fight ventricle of a patient's heart. When the sensed pressure falls below a preset threshold, the device determines the presence of an arrhythmia and a therapy is delivered. More recent ICD systems rely primarily on an evaluation of the sequence of cardiac event timing intervals from a sensed electrogram (ECG). Various algorithms are applied to the detected timing intervals to determine the presence of an arrhythmia. Ventricular fibrillation is typically detected based strictly on heart rate (or interbeat interval) while tachycardia is detected based on rate along with other parameters such as sudden onset, stability, sensed physiological activity (exercise) and ECG waveform morphology. Certain rate boundaries are programmed into the ICD for each patient and these boundaries set up specific detection zones. These systems are not entirely satisfactory because there is still difficulty in making certain determinations, such as for example distinguishing between ventricular tachycardia and sinus tachycardia. It would therefore be desirable to have another detection system which could be used independently or in conjunction with prior art detection systems.

It is known that when an ICD is implanted in each individual patient, the defibrillation threshold should be determined and the defibrillation therapy to be delivered should be programmed with a safety margin. This is necessary because the energy required to defibrillate the heart may change due to changes in lead impedance over time and differences in the defibrillation threshold for spontaneous fibrillation as opposed to the induced fibrillation which is used during testing at the time of implant. The defibrillation threshold may also be different because some fibrillation events in a patient may be more severe than other events. This may be due, among other reasons, to the different possible initiating events for a fibrillation episode. By characterizing the seriousness or severity of a fibrillation event, the energy delivered for defibrillation may be modified to reduce the energy delivered for less severe episodes. A great deal of information for characterizing a fibrillation episode exists in the ECG signal, if it can be extracted and analyzed.

The most common type of mathematical transform for studying signals is the Fourier transform. It looks at all the data available from a particular signal, image, etc. and finds the probability of any individual frequency occurring in the signal. In this way, a signal is represented as the sum of its frequencies. A large amount of data from a signal may be compressed and certain information which may be hidden in the data may be viewed from a different perspective. The power of this representation diminishes when the signal that one is trying to represent changes its character unpredictably during the course of the signal. Essentially, local information is lost when the global representation of a Fourier transform is attempted. An improved method of performing this type of transform is known as the window Fourier transform. With a window Fourier transform, the time series is divided into small windows in time or in space depending on the nature of the data. The transform is performed to obtain the Fourier spectra of the data at various windows. The problem with this technique is that the uncertainty principle begins to set in. The smaller the window, so designed to better handle the localization of the data, the worse its frequency information becomes.

The uncertainty principle can be minimized using the Gabor transform. This transform makes use of the theorem that the minimum uncertainty is achieved with the Gaussian window. Thus, instead of performing the transform to break the signal down into its basic frequencies represented by a time series of sine and cosine functions, a Gaussian function is used. This improves the Fourier transform but still cannot give the detailed information of the time series.

A relatively new mathematical tool for performing this type of signal analysis is the wavelet transform. Wavelets represent a signal in a way that provides local frequency information for each position within the signal. Thus, the wavelet transform can be used to extract information of the time series which is not restricted to the sine or cosine functions. Essentially, the investigator has the freedom to choose any function which is appropriate for obtaining the relevant information of the time series. The advantage is that the signal can be observed at any time scale, i.e., the technique can zoom in on the signal, up to its finest resolution.

It is an object of the present invention to provide a method of characterizing fibrillation.

It is a further object of the invention to provide an ICD utilizing more efficient defibrillation energy delivery.

SUMMARY OF THE INVENTION

The present invention provides a system and method for characterizing cardiac fibrillation using wavelet transforms. By characterizing the seriousness of a fibrillation event, a defibrillation shock may be delivered to the heart with less excess energy than conventional ICDs. A wavelet transform which looks at the second derivative of the time series of a fibrillation event is performed on a digitized ECG to provide a spectral function of the ECG signal. The results are analyzed for "missing peaks" in the data. The more serious the fibrillation, the more peaks will be missing from the data. This information may then used to modify the voltage of the defibrillation shocks as a function of the seriousness of the fibrillation.

BRIEF DESCRIPTION OF THE DRAWINGS

The various features and advantages of the present invention may be more readily understood with reference to the following detailed description taken in conjunction with the accompanying drawings in which.

DETAILED DESCRIPTION OF THE INVENTION

Figure 1A:
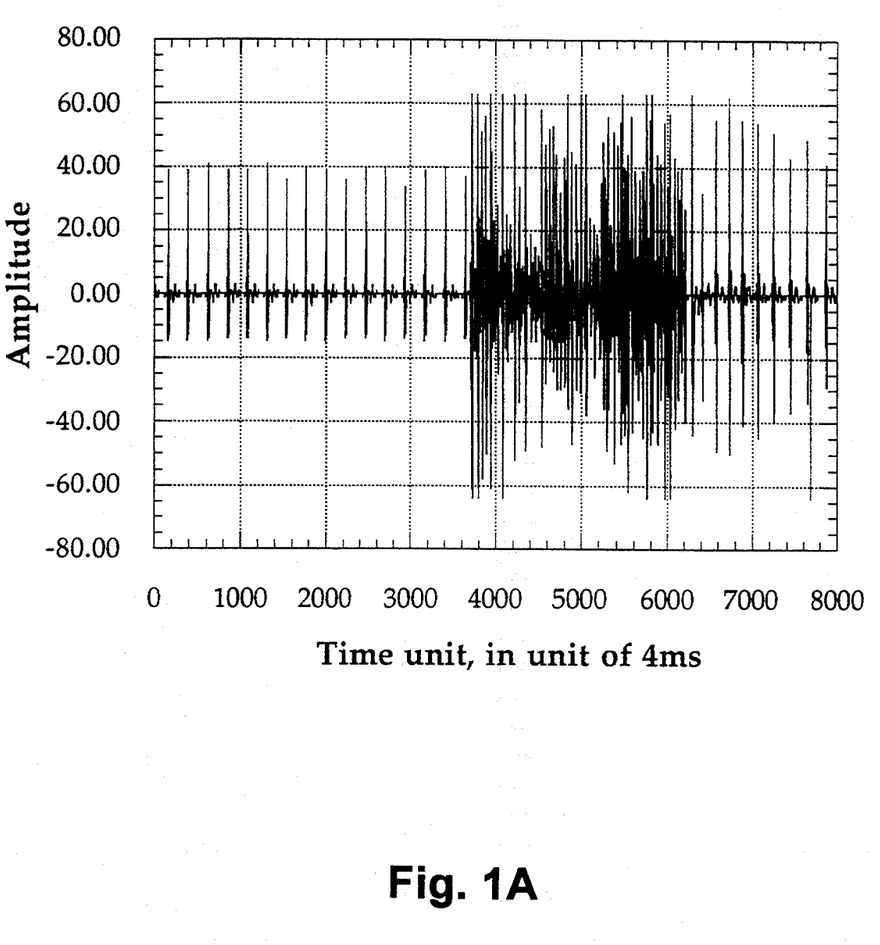
FIG. 1A shows a portion of an internal ECG of a patient as a spontaneous fibrillation event occurs.
Figure 1B:
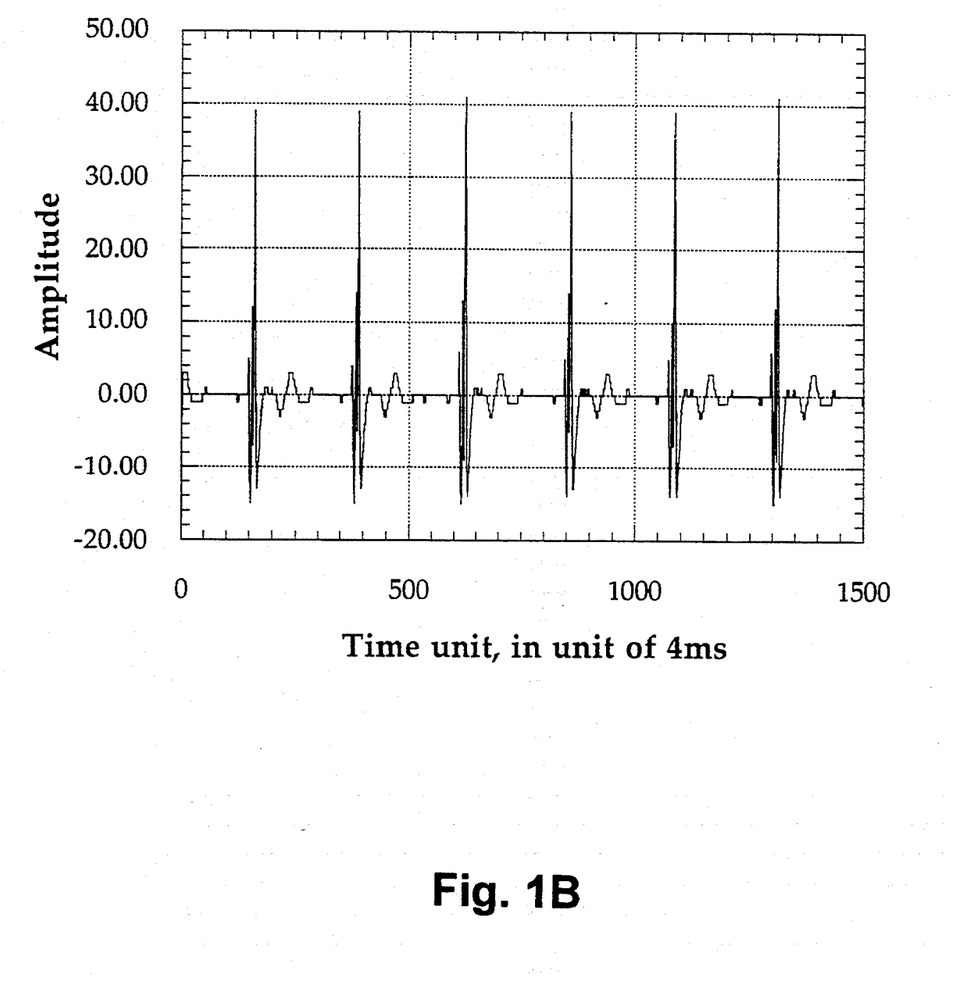
FIG. 1B shows a portion of the first 1500 data points of FIG. 1A.
Figure 1C:
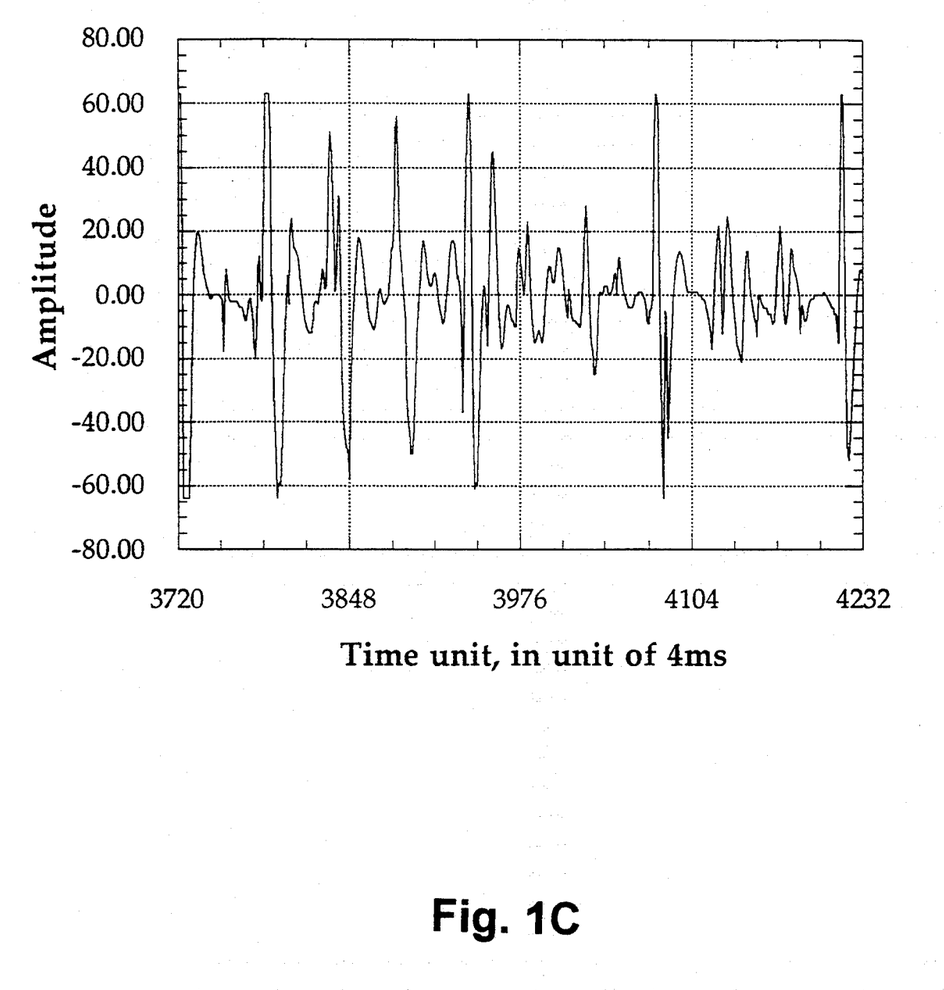
FIG. 1C shows a portion of the signal of FIG. 1A and focused on a portion of the fibrillation event.

The present invention characterizes the seriousness of fibrillation episodes by performing a wavelet transform on the ECG signal of a patient in fibrillation. For purposes of this description, the time series of the ECG signal will be denoted as f(t) and the zoom point in the series will be denoted as T. This is the digitized form of the ECG which has been processed through an analog-to-digital converter. A time series of a fibrillation event is shown in FIG. 1A, which shows about 24 seconds of an ECG signal for a spontaneous fibrillation event as it transitions from a sinus rhythm, FIG. 1B (about 65 beats per minute), to fibrillation. The time scale shown is for an ECG which is sampled every 4 milliseconds. The amplitude of the signal is an arbitrary scale which changes based on sensor sensitivity and the setting of an automatic gain control circuit. For purposes of performing the wavelet transform, a portion of the fibrillation signal is selected and shown on an expanded time scale in FIG. 1C starting at data point 3720 from FIG. 1A. The beginning of the plot in FIG. 1C is the zoom point and is designated as "0" in FIG. 1C. The spectral function S(s,T) which provides the desired information about the ECG signal may be calculated as:

$$S(s,T) = \int f(t)(1/\sqrt{s})W[(t-T)/s]dt$$

where the integration is performed over the selected time domain. In this transform, the function W can be chosen to pick out any interesting information of the time series f(t) for the heart fibrillation data. There are thus several ways of choosing the weight function for the wavelet transform which is to be used. For use with the fibrillation signal, the second derivative of the signal is chosen. The weight function selected for the preferred embodiment, W[(t-T)/s], thus depicts the normalized second derivative of the time series f(t) and may be written as:

$$W(s,T) = ((t/s)^2 - \tfrac{1}{2})exp(-(t/s)^2)$$

where s is the scale factor. The smaller the value of s, the smaller the domain of the time scale which is being viewed or "zoomed in on." The inverse, 1/s, can be considered as the frequency.

Figure 2:
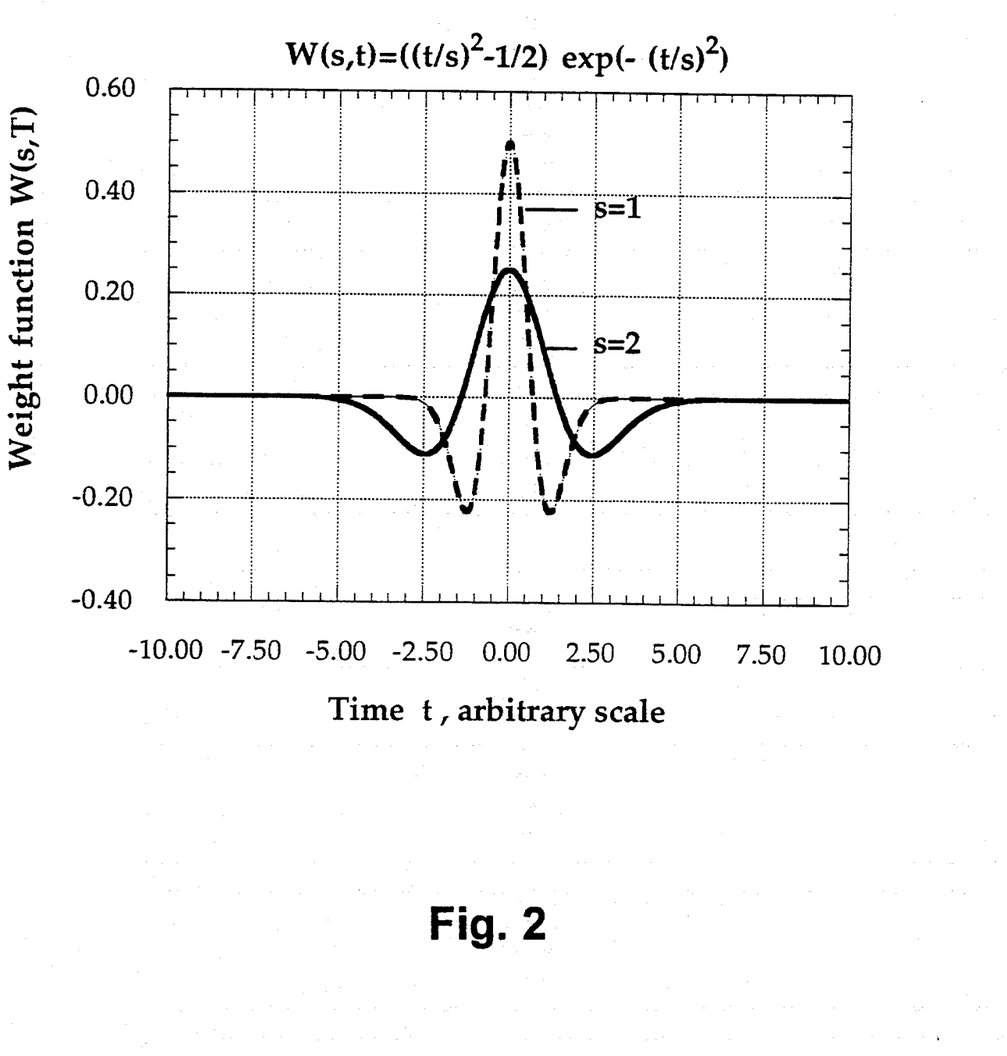
FIG. 2 shows a plot of the weight function used in the wavelet transform for two different scale factors.
Figure 3:
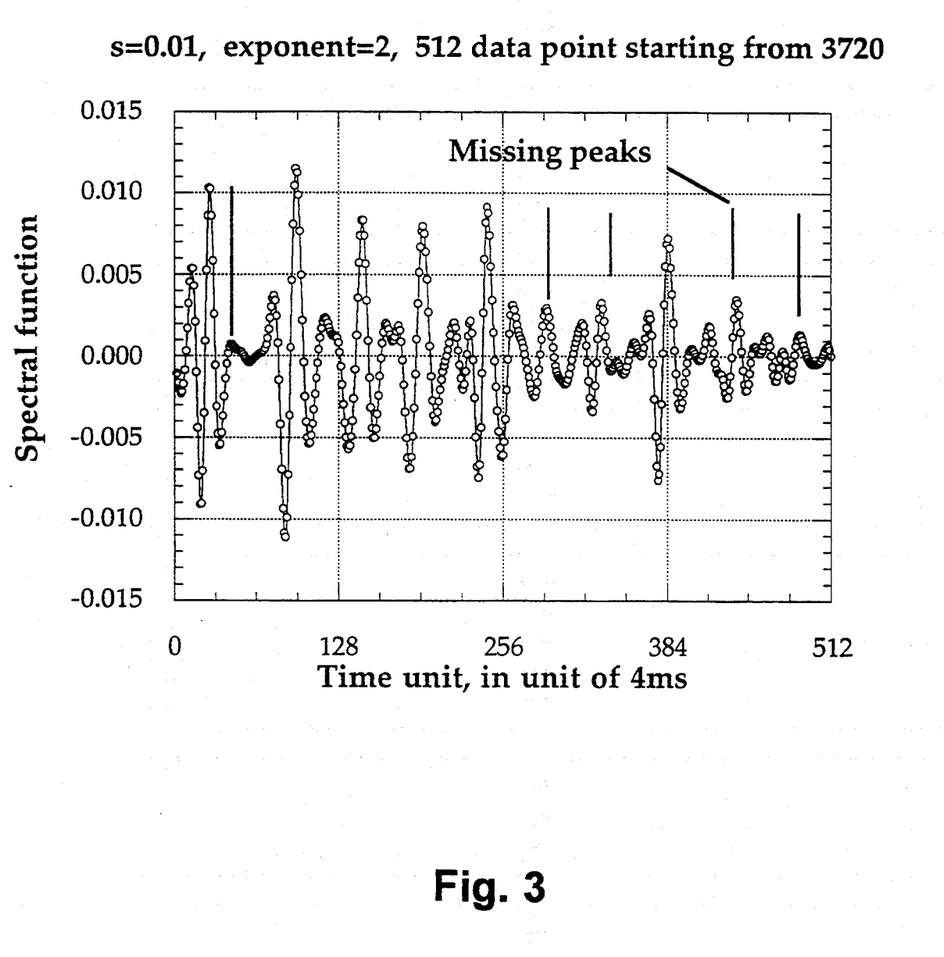
FIG. 3 shows a plot of a wavelet transform performed on the ECG signal of FIG. 1C with missing peaks identified.

The weight function W(s,T) is depicted in FIG. 2 for two different scale factors, s=1 and s=2. The function is symmetric in time around reference time T which is selected (normalized) to be "0". As can be seen, the main parameter which determines the characteristic of the wave function is s. For smaller s, the higher frequency portion of he time system can be probed. For larger values of s, the low frequency domain may be probed. When this transform is applied to the time series with a window of 512 time steps, starting at any point in the fibrillation data, the spectral function S will give a series of spikes of equal spacing. For the data of FIGS. 1A–C, the spacing between main peaks is about 49.5 data points × 4 milliseconds apart = 198 milliseconds. The wavelet transform of the ECG data of FIG. 1C is shown in FIG. 3. The scale s=0.01. As can be seen from the plot, a number of peaks (marked with vertical lines) are missing from the data. It has been discovered that there exists equal spacing spikes for the high frequency regions. This technique has been used to study data of different fibrillation episodes and it has been observed that some of the spikes are missing for the transform data. The number of missing spikes can be correlated to the severity of the fibrillation episode and thus to the amount of energy required for defibrillation to terminate the fibrillation event.

Figure 4:
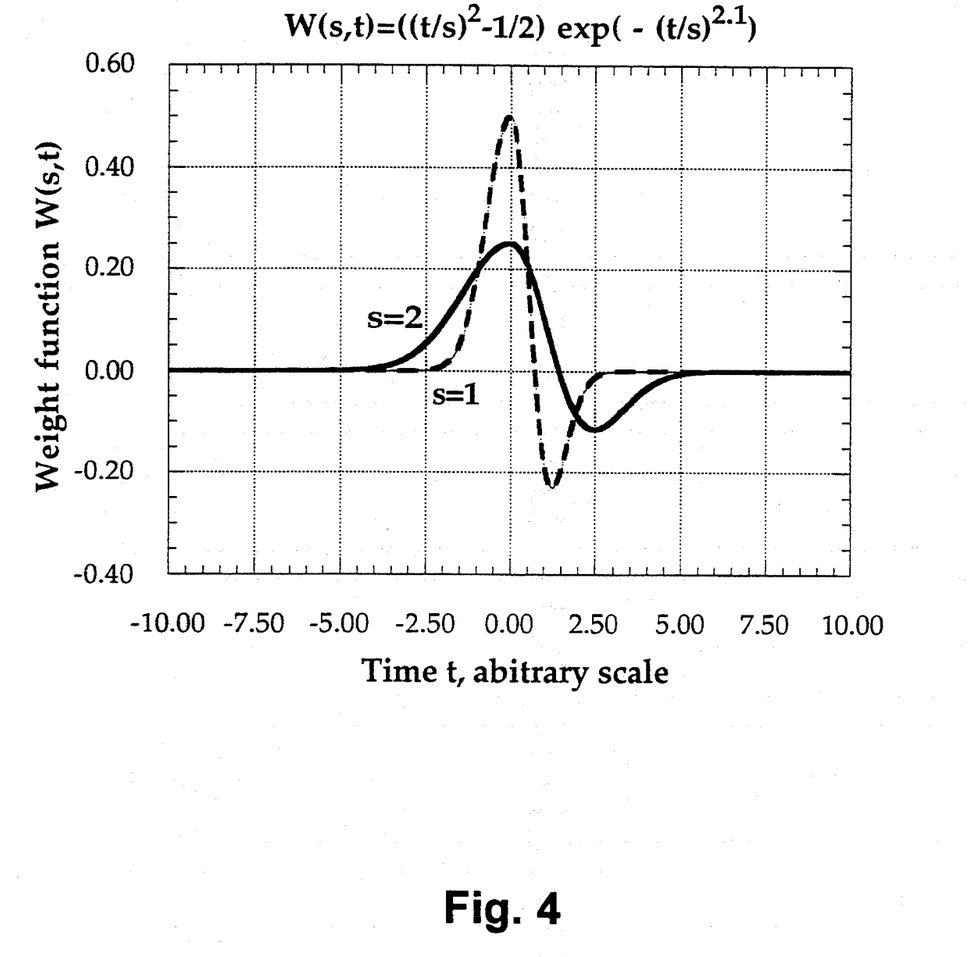
FIG. 4 shows an alternative "skewed" weight function which may be used to study the ECG signal.
Figure 5:
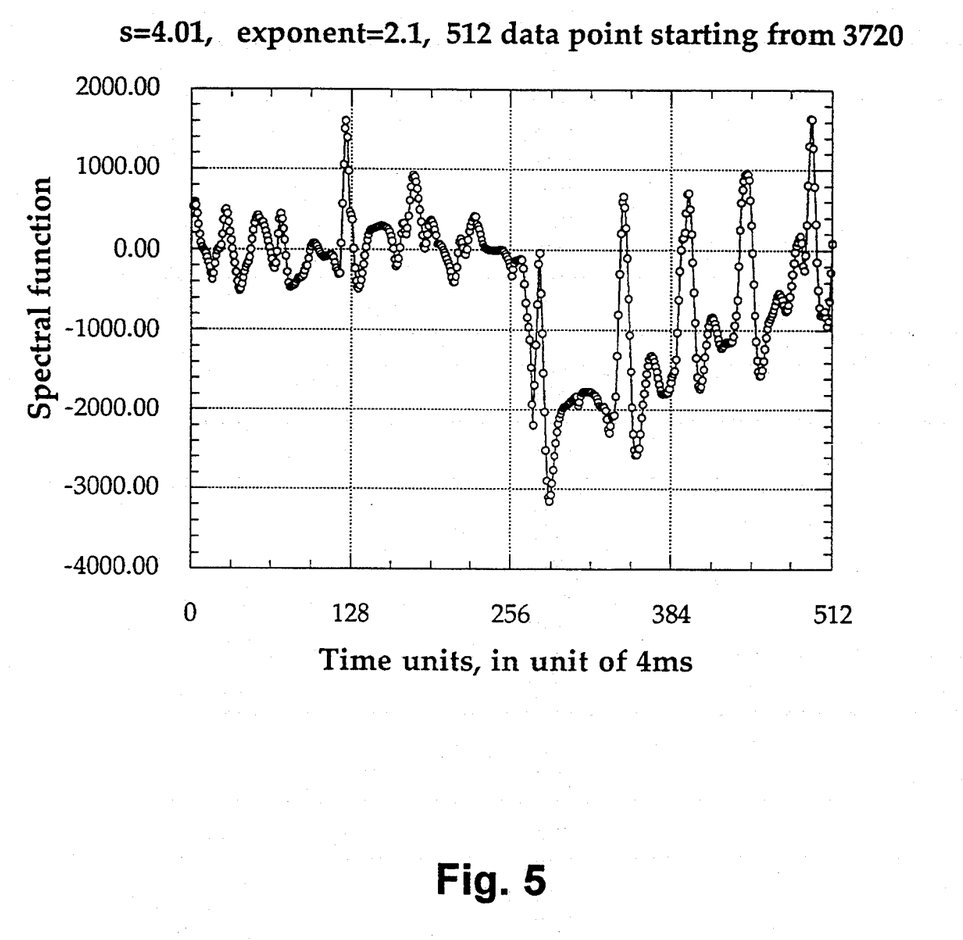
FIG. 5 shows a plot of a wavelet transform performed on the ECG signal of FIG. 4.

In order to confirm that the missing peaks are in fact as marked and not some artifact of the signal, a wavelet transform using a somewhat different weight function may be performed. FIG. 4 shows a skewed weight function where the exponential component is raised to the power of 2.1 rather than 2. FIG. 5 provides the spectral function using the weight function of FIG. 4 and clearly shows that the "missing peaks" are real. The scale factor for this case is 4.01 which is optimum for identifying the missing peaks. The large number of low amplitude or "missing peaks" confirms that this particular fibrillation event is serious and should be treated with more aggressive therapy from the beginning. Fibrillation events which are less serious (fewer missing peaks) may be initially treated with less aggressive therapy.

The wavelet transform can be performed in either software or hardware with a conventional ICD such as the one described in U.S. Pat. No. 5,014,701 to Hess et al. A software program for practicing the invention is presented in Appendix A. Once the wavelet transform has been performed, the spacing of threshold crossings of the transform data is observed for a predetermined time. The number of spikes which are counted is subtracted from the expected number (the predetermined time divided by 188 ms) and this number determines the severity of the fibrillation. The smaller the number, the less severe the episode. The voltage to which the ICD high voltage capacitors are charged is then determined and defibrillation therapy is delivered.

It should be understood that various alternatives to the embodiments of the invention described herein may be employed in practicing the invention. For example, the system and method of the invention can be used in an external defibrillator. Other wavelet transform functions may be used to represent the ECG data. It is thus intended that the following claims define the scope of the invention and that structures and methods within the scope of these claims and their equivalents be covered thereby.

What is claimed is:

1. A method of quantifying cardiac fibrillation comprising the steps of:
    (a) sensing the electrical signals of a patient's heart to provide an ECG signal;
    (b) detecting the presence of a fibrillation event;
    (c) performing a wavelet transform on the fibrillation event in said ECG signal; and
    (d) analyzing the resultant wavelet transform by searching for an absence of signal spikes to characterize the fibrillation event.

2. The method of claim 1 and further including the step of generating an output to modify a voltage to which one or more high voltage capacitors of an implantable defibrillator are charged based on a detected number of missing spikes.

3. The method of claim 1 wherein said wavelet transform is characterized by a function which is a second derivative of said ECG signal.

4. The method of claim 3 wherein a spectral function of said ECG signal is generated by performing said wavelet transform using an equation:

$$S(s,T) = \int f(t)(1/\sqrt{s})W[(t-T)/s]dt$$

where S(s,T) is a spectral function, f(t) is an ECG time series during fibrillation, T is a zoom point of the time series, s is a scale factor, and W[(t-T)/s] is the second derivative function.

5. The method of claim 1 and further including the step of digitizing said ECG signal.

6. A device for characterizing fibrillation of a patient's heart comprising:
means for sensing an ECG signal from said patient's heart;
means for performing a wavelet transform on said ECG signal; and
means for analyzing a resultant transform for an absence of characteristic spikes.

7. A device according to claim 6 wherein said means for analyzing and said means for performing a wavelet transform include a microprocessor.

8. A method for characterizing fibrillation in an ECG signal to determine a level of seriousness of an arrhythmia comprising the steps of:
(a) sensing an ECG signal from a patient's heart;
(b) performing a wavelet transform characterized by a second derivative function for a predetermined frequency range on a series of QRS complexes from the ECG of the patient during fibrillation to provide a resultant transform;
(c) determining a number of missing peaks in the resultant transform; and
(d) characterizing the seriousness of the fibrillation based on the number of missing peaks.

9. The method of claim 8 and further including the step of digitizing said ECG signal.

10. An implantable defibrillator system comprising:
electrode means adapted to be coupled to a patient's heart for use in sensing electrical signals from said patient's heart;
sensing means having an input connected to said electrode means for sensing analog ECG heart signals;
analog-to-digital means for converting the analog ECG heart signal into a digitized ECG heart signal; and
fibrillation characterizing means for characterizing a level of severity of a fibrillation signal including means for performing a wavelet transform on said digitized ECG signal to provide a resultant transform and for analyzing the resultant transform for an absence of characteristic peaks.

* * * * *